United States Patent
Velasquez et al.

(10) Patent No.: US 11,273,434 B2
(45) Date of Patent: Mar. 15, 2022

(54) REGENERATION METHOD OF SOLID CATALYST

(71) Applicants: THE PROCTER & GAMBLE COMPANY, Cincinnati, OH (US); NIPPON SHOKUBAI CO., LTD., Osaka (JP)

(72) Inventors: Juan Estaban Velasquez, Cincinnati, OH (US); Dimitris Ioannis Collias, Cincinnati, OH (US); Jane Ellen Godlewski, Cincinnati, OH (US); Motosuke Imada, Osaka (JP); Koji Shingubara, Osaka (JP); Masashi Tonoya, Osaka (JP); Shinji Kanbara, Osaka (JP); Masaki Okada, Osaka (JP); Tomoharu Oku, Osaka (JP); Hideaki Tsuneki, Osaka (JP); Masanori Nonoguchi, Osaka (JP)

(73) Assignees: THE PROCTER & GAMBLE COMPANY, Cincinnati, OH (US); NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 15/726,897

(22) Filed: Oct. 6, 2017

(65) Prior Publication Data
US 2019/0105651 A1   Apr. 11, 2019

(51) Int. Cl.
| | |
|---|---|
| *B01J 38/16* | (2006.01) |
| *B01J 38/02* | (2006.01) |
| *B01J 38/06* | (2006.01) |
| *B01J 27/182* | (2006.01) |
| *B01J 27/28* | (2006.01) |
| *C07C 51/377* | (2006.01) |

(52) U.S. Cl.
CPC .............. *B01J 38/16* (2013.01); *B01J 27/182* (2013.01); *B01J 27/285* (2013.01); *B01J 38/02* (2013.01); *B01J 38/06* (2013.01); *C07C 51/377* (2013.01)

(58) Field of Classification Search
CPC ........ B01J 38/16; B01J 27/182; B01J 27/285; B01J 38/02; B01J 38/06; C07C 51/377; Y02P 20/584
See application file for complete search history.

(56) References Cited

U.S. PATENT DOCUMENTS

| | | | |
|---|---|---|---|
| 2008/0134888 A1* | 6/2008 | Chao ..................... | B01J 20/041 95/134 |
| 2013/0018161 A1* | 1/2013 | Ezawa ..................... | B01J 27/16 526/317.1 |
| 2013/0225895 A1* | 8/2013 | Quevedo Enriquez ... | C07C 1/20 585/640 |

FOREIGN PATENT DOCUMENTS

| | | |
|---|---|---|
| JP | 2014-518874 | 8/2014 |
| JP | 2015-510885 | 4/2015 |
| RU | 2 238 259 | 7/2003 |
| RU | 2 235 592 | 9/2004 |
| WO | 2013/134385 | 9/2013 |
| WO | 2013/155295 | 10/2013 |

OTHER PUBLICATIONS

Koretsky, Steam Tables—Engineering and Chemical Thermodynamics, 2004, John Wiley & Sons (Year: 2004).*
Patience et al. "Pressure Calcination of VPO Catalyst" Ind. Eng. Chem. Res. 2007, 46, 4374-4381 (Year: 2007).*

* cited by examiner

*Primary Examiner* — Steven J Bos
*Assistant Examiner* — Syed T Iqbal
(74) *Attorney, Agent, or Firm* — Wenderoth, Lind & Ponack, L.L.P.

(57) ABSTRACT

The present invention aims to provide a regeneration method capable of sufficiently restoring the catalytic performance of a solid catalyst used in a dehydration reaction of lactic acid and derivatives thereof. The present invention relates to a method for regenerating a solid catalyst used in a dehydration reaction of lactic acid and derivatives of lactic acid, the method including a contacting step of bringing a solid catalyst containing a component that forms a molten salt in the presence of steam into contact with oxygen and steam under pressure.

18 Claims, No Drawings

REGENERATION METHOD OF SOLID CATALYST

TECHNICAL FIELD

The present invention relates to a regeneration method of a solid catalyst. Specifically, the present invention relates to a regeneration method of a solid catalyst used in a dehydration reaction of lactic acid and derivatives thereof.

BACKGROUND ART (Meth)acrylic acid (ester) is industrially widely used as a raw material of acrylic resin or hydrophilic resin. (Meth)acrylic acid (ester) is produced by gas-phase contact oxidation of raw materials derived from fossil resources, such as propylene and isobutylene, or by dehydration of hydroxy carboxylic acids such as lactic acid as renewable resources, using a solid catalyst.

In the dehydration of hydroxy carboxylic acids, the dehydration reaction is accompanied by the formation of organic matter deposits such as coke deposits on a solid catalyst, leading to a reduction in the catalytic activity. Therefore, alternation of a dehydration reaction step and a regeneration step of a solid catalyst for burning off coke deposits or the like on a catalyst is commonly known as the efficient and continuous production of (meth)acrylic acid (ester). Further, Patent literature documents 1 and 2 disclose methods of regenerating catalysts used in the production of isoprene under pressure in the presence of steam and oxygen.

CITATION LIST

Patent Literature

Patent Literature 1: RU 2235592
Patent Literature 2: RU 2238259

SUMMARY OF INVENTION

Technical Problem

Catalysts used in dehydration reactions of hydroxy carboxylic acids are known to be regenerated as described above. Such a regeneration step however has a problem. If the dehydration reaction step and the regeneration step of a solid catalyst are alternately repeated and the catalyst is subjected to a regeneration step many times, the catalytic performance of the catalyst cannot be sufficiently restored by a conventional method of burning off coke deposits or the like on the catalyst. As for such a problem, the regeneration method of a catalyst disclosed in Patent literature documents 1 and 2 does not describe a degree of restoration of the catalytic performance.

The present invention has been made in view of the current state of the art described above, and aims to provide a regeneration method capable of sufficiently restoring the catalytic performance of a solid catalyst used in a dehydration reaction of lactic acid and derivatives thereof.

Solution to Problem

As a result of the various investigations of a regeneration method of a solid catalyst used in a dehydration reaction of lactic acid and derivatives thereof, the present inventors have found that even the catalytic performance of a catalyst of not being able to be sufficiently restored by a conventional method of burning off coke deposits or the like on the catalyst can be sufficiently restored by a method for bringing a solid catalyst containing a component that forms a molten salt in the presence of steam into contact with oxygen and steam under pressure even, and that the selectivity to acrylic acid is enhanced and the selectivity to propionic acid is reduced as a result of the restoration of the catalytic performance by this contacting step. Thus, the above-mentioned problems have been admirably solved, leading to completion of the present invention.

That is, the present invention relates to a method for regenerating a solid catalyst used in a dehydration reaction of lactic acid and derivatives thereof, the method including a contacting step of bringing a solid catalyst containing a component that forms a molten salt in the presence of steam into contact with oxygen and steam under pressure.

The present invention is described in detail below.

A combination of two or more of preferred embodiments of the present invention described below is also a preferred embodiment of the present invention.

<Solid Catalyst Regeneration Method>

The solid catalyst regeneration method of the present invention (hereinafter, also referred to only as a regeneration method) includes a contacting step of bringing a solid catalyst containing a component that forms a molten salt in the presence of steam into contact with oxygen and steam under pressure (hereinafter, also referred to only as a contacting step). Through this step, coke deposits generated in the dehydration reaction can be sufficiently burned off, and as a result, the catalytic performance can be sufficiently restored. The reason for this is presumably as follows.

The component that forms a molten salt in the presence of steam contained in the solid catalyst is in equilibrium between a condensed state (solid state) obtained through the elimination of water molecules and a hydrolysis state (all or partly melted state) which is a component with catalytic activity for a dehydration reaction of lactic acid and derivatives thereof. The component with catalytic activity in equilibrium exhibits the catalytic activity for a dehydration reaction of lactic acid and derivatives thereof, and forms a molten salt depending on the temperature. In the conventional regeneration method of burning off coke deposits or the like on a catalyst, catalysts are regenerated through a burning reaction substantially in the absence of sufficient steam. As a result, the equilibrium shifts to a condensed state, and the component with catalytic activity is condensed while incorporating organic matters such as coke generated in the dehydration reaction. Such organic matters are prevented from being in contact with oxygen and not sufficiently burned off, failing to sufficiently regenerate the catalyst. Further, coke insufficiently burned comes to the surface of the solid catalyst again when the component that forms a molten salt contained in the solid catalyst is in a hydrolysis state during dehydration. This coke promotes the generation of propionic acid as a by-product, leading to the deterioration of the selectivity to acrylic acid. On the other hand, since in the regeneration method of the present invention, the equilibrium shifts to a hydrolysis state in the presence of steam introduced under pressure, organic matters still remain on the surface of the catalyst and are in contact with oxygen to be sufficiently burned off. As a result, the amount of propionic acid produced as a by-product is reduced to enhance the selectivity to acrylic acid, leading to more sufficient restoration of the catalytic performance.

The component that forms a molten salt contained in the solid catalyst preferably contains a condensed phosphate disclosed in, for example, JP 2014-518874 T. The condensed phosphate is a condensation compound obtained by dehydration of two or more orthophosphate molecules.

Examples of the condensed phosphate include salts of alkali metals such as lithium, sodium, potassium, rubidium, and cesium; and salts of the elements in Group 2 of the periodic table such as berylium, magnesium, calcium, strontium, and barium. Preferably, the condensed phosphate is an alkali metal salt or a salt of an alkaline-earth metal such as calcium or barium. Examples of the condensed phosphate include $Na_4P_2O_7$, $Na_2H_2P_2O_7$, $(NaPO_3)_n$, $K_4P_2O_7$, $K_2H_2P_2O_7$, $(KPO_3)_n$, $Ca_2P_2O_7$, $CaH_2P_2O_7$, $Ca(PO_3)_2$, $Ca_3(PO_4)_2$, $Ba_2P_2O_7$, $BaH_2P_2O_7$, $Ba(PO_3)_2$, $Ca_{2-x-s}K_{2x}H_{2s}P_2O_7$, and $Ba_{2-x-s}K_{2x}H_{2s}P_2O_7$, wherein n is a positive integer, x and s are each 0 or more and less than 0.5. These condensed phosphates may be used alone or two or more of these may be used.

The condensed phosphate is preferably $K_4P_2O_7$, $K_2H_2P_2O_7$, $(KPO_3)_n$, $Ba_2P_2O_7$, $BaH_2P_2O_7$, $Ba(PO_3)_2$, or $Ba_{2-x-s}K_{2x}H_{2s}P_2O_7$, still more preferably $Ba_2P_2O_7$, $(KPO_3)_n$, or $Ba_{2-x-s}K_{2x}H_{2s}P_2O_7$. The hydrolysis reactions of $Ba_2P_2O_7$ and $(KPO_3)_n$ are exemplary shown in the following as the hydrolysis of a condensed phosphate.

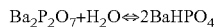

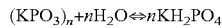

The condensed phosphate is preferably a mixture of an alkali metal salt and an alkaline-earth metal salt, more preferably a mixture of $Ba_2P_2O_7$ and $(KPO_3)_n$.

When a mixture of an alkali metal salt and an alkaline-earth metal salt is used as the condensed phosphate, the molar ratio of the alkali metal to the alkaline-earth metal (alkali metal/alkaline-earth metal) is preferably 0.5 to 2.0, and the molar ratio of phosphorus to the total of the alkali metal and the alkaline-earth metal is preferably 0.7 to 1.7.

The solid catalyst may be in the form of powder or molded body. The molded body may have any shape such as a ball, cylinder, ring, or honeycomb shape. The form of the catalyst can be selected depending on the reaction pattern to be used.

The solid catalyst may be supported on a carrier. Examples of the carrier include silica, diatomite, alumina, silica alumina, silica magnesia, zirconia, titania, magnesia, niobia, ceria, zeolite, silicon carbide, and carbide. The carrier is preferably titania, silica, zirconia, or alumina, more preferably silica or zirconia, still more preferably silica.

The zeolite is an aqueous aluminosilicate containing an alkali metal or an alkaline-earth metal and having a rigid anionic framework and channels (tubular fine pores) and cavities (hollow portions) regularly arranged, and is represented by the general formula $Mx/m[(AlO_2)x(SiO_2)y].zH_2O$, wherein M represents a metal ion, m represents a valence of the metal ion, and x, y, and z each represent a positive integer.

The zeolite has a variety of frameworks represented by framework type codes defined by International Zeolite Association. Examples of the framework type code include LTA, FER, MWW, MFI, MOR, LTL, FAU, and BEA. In particular, LTL is preferred.

The zeolite may be a natural product or may be chemically synthesized. The zeolite may be modified zeolite. The modified zeolite refers to a zeolite modified by replacing part or all of the alkali metal ions or alkaline-earth metal ions of the zeolite with other metal ions or protons by ion exchange, or a zeolite modified by supporting an inorganic salt or the like.

Examples of other metal ions include an alkali metal such as lithium, sodium, potassium, rubidium, or cesium; an alkaline-earth metal such as berylium, magnesium, calcium, strontium, or barium; and a transition metal such as titanium, vanadium, chromium, manganese, iron, cobalt, nickel, copper, or zinc. In particular potassium or barium is preferred.

Examples of the inorganic salt include phosphate, sulfate, nitrate, molybdate, tungstate, stannate, and antimonate. In particular, phosphate is preferred. Further, the preferred embodiments of the inorganic salt include a condensed phosphate as the phosphate.

Examples of the metal ion contained in the phosphate include ions of an alkali metal such as lithium, sodium, potassium, rubidium, or cesium; an alkaline-earth metal such as berylium, magnesium, calcium, strontium, or barium; and a transition metal such as titanium, vanadium, chromium, manganese, iron, cobalt, nickel, copper, or zinc. In particular, potassium or barium is preferred.

The catalyst used in the dehydration reaction of lactic acid and derivatives thereof may be taken out from a reactor and subjected to the contacting step or may be subjected to the contacting step in a reactor for the dehydration reaction without taking out the catalyst from the reactor.

When the contacting step is performed in the reactor for the dehydration reaction of lactic acid and derivatives thereof, a fixed-bed flow reactor filled with a solid catalyst is preferably used as the reactor. In addition, the fixed-bed flow reactor is preferably a multitubular reactor. Since a multitubular reactor has a large heat transfer area, heat generated by burning coke during the regeneration of the catalyst can be efficiently removed.

The partial pressure of the steam in the system (reactor) in the contacting step may be appropriately controlled depending on the type of the catalyst. The partial pressure of the steam is preferably 0.3 to 24 MPa, more preferably 0.3 to 10 MPa, still more preferably 0.3 to 5.0 MPa, particularly preferably 0.3 to 1.0 MPa. When the steam partial pressure in the system falls within the above preferred range, the equilibrium of the component that forms a molten salt in the presence of steam contained in the solid catalyst shifts to a hydrolysis state. Therefore, the removal efficiency of organic matters is further enhanced and the catalytic performance is more sufficiently restored.

The partial pressure in the system (reactor) herein refers to a pressure at an outlet side of the catalyst layer.

The steam partial pressure, the below described oxygen partial pressure, and the entire pressure can be measured using a pressure gauge and a gas concentration meter.

The oxygen partial pressure in the system (reactor) in the contacting step may be appropriately controlled depending on the amount of coke deposits on the catalyst. The oxygen partial pressure is preferably more than 0 MPa and not more than 1.0 MPa.

In the contacting step, the solid catalyst may be brought into contact with oxygen and steam under pressure by any method. Oxygen and steam may be separately introduced into the system filled with the solid catalyst, or a gas mixture of oxygen and steam may be introduced into the system. A gas mixture is preferably introduced. A gas such as air prepared by diluting oxygen with an inert gas such as nitrogen may be used instead of oxygen gas. A gas mixture of steam and air is preferably introduced into the system from the following point of view. The oxygen concentration in the gas mixture can be controlled by controlling the amount of an inert gas such as nitrogen in the gas mixture. As a result, the composition of the gas in the system can be controlled so as not to fall within the explosive range, or the burning rate of coke during the regeneration of the catalyst is controlled to prevent thermal runaway so that the temperature of the catalyst layer can be regulated. These conditions are preferred in terms of the safe operation of regeneration of catalyst.

As a reaction apparatus, a fluidized-bed reaction apparatus is preferred because the flowing state of the solid catalyst in a reactor is controlled by controlling the amount of an inert gas such as nitrogen in the gas mixture so that a uniformly mixed state in the reactor can be achieved. In the fluidized-bed reaction apparatus, there may be usually a uniformly fluidized and mixed state in the reactor. Therefore, the fluidized-bed reaction apparatus is excellent in control or homogenization of the temperature in the reactor, prevention of local overheating in the reactor, or reaction heat recovery. The fluidized-bed reaction apparatus is therefore advantageous to a reaction process having a problem of removal of heat, such as a burning reaction of coke during the regeneration of the catalyst accompanied by the generation of a large amount of heat. Accordingly, the preferred embodiments of the catalyst regeneration apparatus include a fluidized-bed reaction apparatus.

In the contacting step, the oxygen concentration in the gas component other than steam is preferably 50% by volume or less, more preferably 30% by volume or less, still more preferably 25% by volume or less.

The amount of the steam introduced into the system in the contacting step relative to 100% by volume of oxygen introduced into the system is preferably 1% to 100000% by volume, more preferably 10% to 100000% by volume, still more preferably 100% to 100000% by volume.

When the amount of the steam relative to the amount of oxygen falls within the above preferred range, the amounts of steam and oxygen are well balanced, and coke or the like can be sufficiently burned with oxygen while the equilibrium of the component that forms a molten salt contained in the solid catalyst is shifted to a hydrolysis state. Thus, the catalytic performance can be sufficiently restored.

In the contacting step, steam and oxygen each may be introduced into the system at any flow rate, and the flow rates may be appropriately controlled depending on heat build-up from burning of coke in the catalyst layer or the pressure loss in the catalyst layer.

In the contacting step, the contact time of the solid catalyst with oxygen and steam under pressure depends on, for example, the flow rates of steam and oxygen. The contact time is preferably 3 times or less, more preferably 2 times or less, still more preferably 1 time or less, particularly preferably 0.5 times or less of the time to perform the dehydration reaction step. The contact time is usually 0.1 times or more of the time to perform the dehydration reaction step. When the contact time falls within the above preferred range, the productivity of acrylic acid can be more enhanced in the production of acrylic acid by repeating the catalyst regeneration method of the present invention and a below described dehydration reaction of lactic acid and derivatives thereof.

The temperature of the contacting step is preferably appropriately controlled depending on the type of the catalyst to be used. The contacting step is performed at preferably 200° C. to 700° C., more preferably 250° C. to 650° C., still more preferably 300° C. to 600° C., particularly preferably 350° C. to 500° C.

When the contacting step is performed at the above preferred temperature, the component that forms a molten salt contained in the solid catalyst is more sufficiently melt, and organic matters remain on the surface of the solid catalyst. Such organic matters can be sufficiently brought into contact with oxygen and are likely to be removed. Further, when the contacting step is performed at the above preferred temperature, the burning reaction of organic matters sufficiently proceeds to more sufficiently remove the organic matters, and the catalytic performance is therefore sufficiently restored.

The temperature means a temperature of a heating medium such as a salt bath set to control the temperature of the reactor filled with a catalyst.

In the contacting step, the temperature may be kept constant or may be varied. For example, the temperature of a heating medium may be increased after a rise in the temperature due to heat build-up from burning of coke in the catalyst layer peaks. As a result, a rapid rise in the temperature due to rapid burning of coke can be suppressed, and the catalyst can be regenerated at a temperature not higher than the upper temperature limit of the catalyst. A rise in the temperature of the catalyst layer can be observed by measuring and monitoring the temperature of the inside of the catalyst layer.

A rise in the temperature ($\Delta T$) of the catalyst layer in the contacting step is preferably 200° C. or less, more preferably 150° C. or less, still more preferably 100° C. or less.

When the catalyst regeneration method of the present invention is used in the production of acrylic acid in which a cycle of dehydration of lactic acid and derivatives thereof and regeneration of the catalyst is repeated, the catalyst regeneration step in the present invention may be performed whenever a dehydration step of lactic acid and derivatives thereof is performed, or a combination of a dehydration step of lactic acid and derivatives thereof, a conventional catalyst regeneration method of burning off coke deposits or the like on the catalyst, and the catalyst regeneration method of the present invention may be performed.

The high catalytic activity and high selectivity to acrylic acid of the catalyst can be maintained for a long time by the repetition of the catalyst regeneration step in the present invention. As a result, the replacement frequency of the catalyst can be more reduced, leading to a reduction in the production cost of acrylic acid. The repetition of the catalyst regeneration step in the present invention includes the repetition of only the catalyst regeneration step in the present invention and the repetition of a combination of the conventional catalyst regeneration method and the catalyst regeneration method of the present invention.

<Production Method of Acrylic Acid and Derivatives Thereof>

A solid catalyst regenerated by the catalyst regeneration method of the present invention is preferably used in the production of acrylic acid and derivatives thereof (acrylic acid and esters of acrylic acid) by a dehydration reaction of lactic acid and derivatives thereof. That is, the production method of acrylic acid and derivatives thereof preferably includes a dehydration step of lactic acid and derivatives thereof and the solid catalyst regeneration method of the present invention.

The lactic acid and derivatives thereof include at least one compound selected from the group consisting of lactic acid and esters of lactic acid.

The dehydration step is preferably a step of dehydration of lactic acid and derivatives thereof by a gas-phase contact reaction of lactic acid and derivatives thereof with a solid catalyst (catalyst for dehydration).

In the dehydration step, a raw material composition containing at least one compound selected from the group consisting of lactic acid and esters of lactic acid is preferably used as a raw material.

Lactic acid and an ester of lactic acid to be used in the dehydration step may be produced by fermentation or chemically produced.

The raw material composition may contain a solvent. The solvent may be any solvent capable of dissolving lactic acid and esters of lactic acid, and examples thereof include water, alcohols, hydrocarbons, ethers, ketones, esters, amines, and amides. These may be used alone or two or more of these may be used.

The concentration of all the lactic acid and the ester(s) of lactic acid in the raw material composition is preferably 2% to 95% by mass, more preferably 5% to 80% by mass, still more preferably 5% to 50% by mass relative to 100% by mass of the raw material composition.

The raw material composition may contain an oligomer(s) such as a dimer or a trimer of lactic acid or an ester of lactic acid, and the oligomer(s) may be used as a raw material. The amount of the oligomer(s) in the raw material composition is preferably 0.01% to 20% by mass, more preferably 0.1% to 10% by mass relative to 100% by mass of the lactic acid, the ester(s) of lactic acid, and the oligomer(s). At an amount of the oligomer(s) of 0.01% by mass or more, oligomerization of the lactic acid and the ester(s) of lactic acid can be suppressed or the amount of oligomers thereof can be reduced by only minimal equipment or minimum energy. At an amount of the oligomer(s) of 20% by mass or less, the generation of carbonaceous materials (organic matters) on a dehydration catalyst and clogging due to caulking are suppressed, leading to enhancement of the selectivity to acrylic acid and derivatives thereof.

In the dehydration step, the same catalyst as the solid catalyst used in the regeneration method of the present invention may be used.

Any reaction apparatus may be used in the dehydration step, and examples thereof include a stirring reactor, a fixed-bed flow reactor, a fluidized-bed reactor, and an entrained-bed reactor. A fixed-bed flow reactor filled with a solid catalyst is preferred.

The fixed-bed flow reactor is preferably a multitubular reactor equipped with plural reaction tubes. Preferably, acrylic acid and derivatives thereof are produced by dehydrating lactic acid and ester(s) of lactic acid by a gas-phase contact reaction while a gas component of lactic acid and ester(s) of lactic acid is passed through the reaction tubes as a raw material.

The preferred embodiments include a switching reactor in which plural reactors are connected in parallel and each reactor is appropriately switchable between a dehydration reaction step and a regeneration step. In this case, the reaction step and the regeneration step can be simultaneously performed, and the high productivity can be maintained.

The reaction temperature in the dehydration step may be appropriately controlled depending on the type of a catalyst to be used, and is usually 120° C. to 700° C., preferably 300° C. to 450° C. The "reaction temperature" in the gas-phase dehydration reaction means a temperature of a heating medium or the like set to control the temperature of the reactor. Similarly, the reaction pressure of the dehydration reaction may be appropriately controlled, and is preferably more than 0 MPa and not more than 5.0 MPa, more preferably 0.1 to 2.5 MPa.

When the gas-phase dehydration reaction of lactic acid is performed using a fixed-bed flow reactor, the flow rate of a reactant gas to be introduced into the fixed-bed flow reactor is preferably appropriately controlled in consideration of the concentration of a raw material, the amount of carrier gas, the performance of catalyst, or productivity. When the flow rate is represented by a gas hourly space velocity (GHSV) per catalyst unit volume, the flow rate is usually 50 to 36000 $h^{-1}$, preferably 100 to 10000 $h^{-1}$, more preferably 150 to 6000 $h^{-1}$.

Advantageous Effects of Invention

The solid catalyst regeneration method of the present invention has the features as described above, and is capable of sufficiently burning off coke deposits on a catalyst in a dehydration step. As a result, the selectivity to propionic acid generated as a by-product during the dehydration reaction is reduced to enhance the selectivity to acrylic acid that is mainly produced, leading to sufficient restoration of the catalytic performance. Further, the expansion of the catalyst or the reduction in strength of the catalyst due to coke deposits on the catalyst is suppressed, and the breakage or pulverization of the catalyst can be prevented. Since propionic acid produced as a by-product is difficult to separate from acrylic acid by distillation, a multistage crystallization step is needed to remove propionic acid, leading to an increase in cost of the purification process of acrylic acid. In the regeneration method of the present invention, the amount of propionic acid produced as a by-product can be sufficiently reduced, leading to a reduction in cost of the purification of acrylic acid. Further, the high catalytic activity and the selectivity to acrylic acid of the catalyst can be maintained for a long time by the repetition of the solid catalyst regeneration method of the present invention. Therefore, the replacement frequency of the catalyst can be reduced, leading to a reduction in the production cost of acrylic acid. In view of these effects, the solid catalyst regeneration method of the present invention is suitable for the production of acrylic acid or the like.

DESCRIPTION OF EMBODIMENTS

The present invention is described in more detail below with reference to, but not limited to, the following examples. Unless otherwise specified, "parts" means "parts by weights", and "%" means "% by mass".

<Measurement of Amount of Coke Remaining on Solid Catalyst>

A catalyst was heated in the air using a differential high temperature differential thermal balance (TG-DTA2020SA, Bruker AXS), and the amount of coke on the catalyst was calculated from the weight reduction.

Production Example 1: Production of Catalyst

A potassium metaphosphate-barium pyrophosphate (molar ratio:K/Ba/P=0.4/0.6/1.0) powder was prepared with reference to Example 1 in JP 2014-518874 T. To the resulting potassium metaphosphate-barium pyrophosphate powder was added an inorganic carrier component and a binder containing 122% by mass of $SiO_2$. The resulting mixture was extruded and molded into a 4 mm diameter article, and cut into pellets with a 4 mm length. The pellets were burned in an air atmosphere at 600° C. for 12 hours. Thus, a catalyst was obtained.

Production Example 2: Production of Acrylic Acid

Acrylic acid was produced by the dehydration of lactic acid through a gas-phase fixed-bed flow reaction system under pressure using the catalyst prepared in Production Example 1.

First, a titanium-coated stainless-steel reaction tube (inner diameter: 24.5 mm, length: 620 mm) was filled with 142 mL of the catalyst to prepare a fixed-bed flow reactor, and then this reactor was immersed in a salt bath at 375° C. Thereafter, nitrogen gas was circulated in the reactor at a flow rate of 0.70 NL/min for 30 minutes, and the pressure was increased to 0.50 MPa. The supply of nitrogen gas was stopped after the pressure in the reactor was stabilized, and a reactant gas of a 35% by mass aqueous solution of lactic acid (the composition of the reactant gas:lactic acid 10 mol %, water 90 mol %) was circulated at a flow rate (GHSV) of 480 hr$^{-1}$ for 48 hours.

After the reactant gas was circulated in the reactor, the flowing gas was condensed to a liquid by cooling and collected. The liquid was drawn at specific time intervals. Hereinafter, the liquid condensed by cooling and drawn refers to an "effluent". Part of the effluent was taken and qualitatively and quantitatively analyzed using a gas chromatography (GC) apparatus (GC-2010, Shimadzu Corporation) equipped with a FID detector and a liquid chromatography (LC) apparatus (ACQUITY UPLC system, Waters) equipped with a UV detector. The quantitative analysis by GC or LC was performed by an internal standard method. Acrylic acid and by-products such as propionic acid were analyzed by GC, and lactic acid was analyzed by LC. The conversion of lactic acid (LA conversion), selectivity to acrylic acid (AA selectivity), and selectivity to propionic acid (PA selectivity) were calculated from the results of the quantitative analysis using the following equations.

LA conversion=(1−(the number of moles of lactic acid in effluent)/(the number of moles of lactic acid supplied to reactor))×100

AA selectivity=(((the number of moles of acrylic acid in effluent)/(the number of moles of lactic acid supplied to reactor))×100)/(conversion of lactic acid×100)

PA selectivity=(((the number of moles of propionic acid in effluent)/(the number of moles of lactic acid supplied to reactor))×100)/(conversion of lactic acid×100)

Reference Example: Regeneration of Solid Catalyst in the Absence of Steam and Production of Acrylic Acid Acrylic acid was produced in accordance with Production Example 2, and the production was stopped after 48 hours from the start of the production. The catalyst was left in the reactor. Thereafter, the pressure was returned to atmospheric pressure while only nitrogen gas was circulated in the fixed-bed flow reactor at a flow rate of 0.70 NL/min for 1 hour, and a reactant gas and a product gas remaining in the reactor were discharged. Thereafter, while the pressure was maintained at atmospheric pressure and the temperature of the salt bath was maintained at 375° C., a gas mixture of nitrogen at a flow rate of 0.60 NL/min and air at a flow rate of 0.10 NL/min was circulated in the reactor for 15 minutes, and subsequently, a gas mixture of nitrogen at a flow rate of 0.40 NL/min and air at a flow rate of 0.30 NL/min was circulated for 45 minutes. Then, only air was circulated at a flow rate of 0.70 NL/min for 23 hours, and carbonaceous deposits (organic matter deposits) or the like on the catalyst were burned off. Thus, the catalyst was regenerated.

After the cycle of the production of acrylic acid and the regeneration of the catalyst in the absence of steam was repeated six times (cycles), the seventh production of acrylic acid was performed for 48 hours. The LA conversion, AA selectivity, and PA selectivity in each cycle were shown in Table 1. The conditions of the regeneration of the solid catalyst were shown in Table 2.

Table 1 shows that in the seventh production of acrylic acid after the repetition of the regeneration of the solid catalyst in the absence of steam, the selectivity to acrylic acid significantly deteriorated, and the selectivity to propionic acid significantly increased.

TABLE 1

| Cycle | Production time of acrylic acid (h) | LA conversion [%] | | | AA selectivity [%] | | | PA selectivity [%] | | |
|---|---|---|---|---|---|---|---|---|---|---|
| | | 1 h | 48 h | Ave. | 1 h | 48 h | Ave. | 1 h | 48 h | Ave. |
| 1 | 0-48 | 98.5 | 94.5 | 96.5 | 80.8 | 79.4 | 84.3 | 0.3 | 1.6 | 0.9 |
| 2 | 48-96 | 94.1 | 90.9 | 92.9 | 83.7 | 77.6 | 78.4 | 0.8 | 2.2 | 1.7 |
| 3 | 96-144 | 96.0 | 91.9 | 94.1 | 84.9 | 78.6 | 81.4 | 0.7 | 2.0 | 1.5 |
| 4 | 144-192 | 96.7 | 91.4 | 94.3 | 85.0 | 78.7 | 82.0 | 0.8 | 1.9 | 1.3 |
| 5 | 192-240 | 95.9 | 90.2 | 93.8 | 83.2 | 77.4 | 80.9 | 0.6 | 1.7 | 1.2 |
| 6 | 240-288 | 96.3 | 93.1 | 94.3 | 84.4 | 85.9 | 84.8 | 1.1 | 2.3 | 1.5 |
| 7 | 288-336 | 96.6 | 93.5 | 95.7 | 75.9 | 70.9 | 72.9 | 2.3 | 2.5 | 2.3 |

Example 1: Regeneration of Solid Catalyst in the Presence of Steam and Production of Acrylic Acid The seventh production of acrylic acid in Reference Example was stopped after 48 hours from the start of the production. The catalyst was left in the reactor. Thereafter, the pressure was returned to atmospheric pressure while only nitrogen gas was circulated in the fixed-bed flow reactor at a flow rate of 0.70 NL/min for 1 hour, and a reactant gas and a product gas remaining in the reactor were discharged. Thereafter, the pressure was increased to 0.55 MPa. The temperature of the salt bath was maintained at 375° C., and the supply of nitrogen gas was stopped after the internal pressure of the reactor was stabilized. Then, a mixture of steam at a flow rate of 1.3 g/min and air at a flow rate of 0.35 NL/min was circulated for 24 hours, and carbonaceous deposits or the like on the catalyst were burned off. Thus, the catalyst was regenerated. The temperature of the salt bath in which the fixed-bed flow reactor was immersed was increased to 450° C. in 6 hours from the start of the circulation of steam, and the temperature was maintained. The conditions of the regeneration of the solid catalyst were shown in Table 2.

Subsequently, the temperature of the salt bath was reduced to 375° C., and acrylic acid was continuously produced for 48 hours in accordance with Production Example 2. The LA conversion, AA selectivity, and PA selectivity in the production of acrylic acid were shown in Table 3.

The amount of coke remaining on the regenerated catalyst was measured. The result was shown in Table 4. The amount of the coke remaining was calculated from the following equation.

Amount of coke remaining (% by mass)=reduced weight determined by TG analysis/weight of regenerated catalyst×100

After the production of acrylic acid, the catalyst was regenerated again and taken out from the reactor. The crushing strength of the catalyst was measured using a compact table-top universal tester (EZ Test, Shimadzu Corporation) to be 170 N on average. The lateral strength of each pellet was measured.

Example 2: Regeneration of Solid Catalyst in the Presence of Steam and Production of Acrylic Acid A solid catalyst was regenerated and acrylic acid was produced as in Example 1 except that the pressure during the regeneration was 0.40 MPa and the flow rates of steam and air were 0.83 g/min and 0.35 NL/min, respectively. The conditions of the regeneration of the solid catalyst were shown in Table 2. The LA conversion, AA selectivity, and PA selectivity in the production of acrylic acid were shown in Table 3.

Comparative Example 1: Regeneration of Solid Catalyst in the Absence of Steam and Production of Acrylic Acid The seventh production of acrylic acid in Reference Example was stopped after 48 hours from the start of the production. Thereafter, the solid catalyst was regenerated under the same catalyst regeneration conditions as in the first to sixth regeneration treatments in Reference Example.

Subsequently, acrylic acid was continuously produced for 48 hours in accordance with Production Example 2. The LA conversion, AA selectivity, and PA selectivity in the production of acrylic acid were shown in Table 3.

The amount of coke on the regenerated catalyst was measured as in Example 1. The results were shown in Table 4.

After the production of acrylic acid, the catalyst was regenerated again and taken out from the reactor. The crushing strength of the catalyst measured was 150N on average. The result demonstrates that the strength of the catalyst was lower than the strength of the catalyst in Example 1.

TABLE 2

|  | $P_{total}$ [MPa] | Steam in regenerated gas [vol %] | $P_{H2O}$ [MPa] | Reaction temperature (temperature of salt bath) [° C.] |
|---|---|---|---|---|
| Example 1 | 0.55 | 82 | 0.45 | 375-450 |
| Example 2 | 0.40 | 75 | 0.3 | 375-450 |
| Comparative Example 1 | 0.10 | 0 | 0 | 375 |

TABLE 3

|  | Production time of acrylic acid (h) | LA conversion [%] | | | AA selectivity [%] | | | PA selectivity [%] | | |
|---|---|---|---|---|---|---|---|---|---|---|
|  |  | 1 h | 48 h | Ave. | 1 h | 48 h | Ave. | 1 h | 48 h | Ave. |
| Example 1 | 336-384 | 98.8 | 97.9 | 98.4 | 80.6 | 79.8 | 81.3 | 1.1 | 1.5 | 1.3 |
| Example 2 | 336-384 | 98.0 | 96.2 | 97.0 | 78.8 | 75.6 | 77.1 | 1.5 | 2.0 | 1.8 |
| Comparative Example 1 | 336-384 | 96.5 | 93.5 | 95.6 | 72.0 | 68.3 | 70.1 | 2.5 | 2.8 | 2.6 |

TABLE 4

|  | Amount of coke remaining (% by mass) |
|---|---|
| Reference Example (catalyst after 7 cycles of reaction) | 3.0 |
| Example 1 | 0.3 |
| Comparative Example 1 | 0.9 |

As is clear from the comparison between the amounts of coke on the regenerated catalysts in Example 1 and Comparative Example 1 shown in Table 4, coke was burned off more efficiently in Example 1 than in Comparative Example 1. Further, Table 3 showed that the selectivity to acrylic acid was more enhanced and the selectivity to propionic acid was more reduced in Examples 1 and 2 in which the regeneration was performed in the presence of steam than in Comparative Example 1.

These results demonstrate that in the solid catalyst regeneration method of the present invention, coke deposits on a catalyst can be sufficiently burned off by regeneration treatment of bringing the catalyst into contact with oxygen and steam under pressure, the selectivity to propionic acid produced as a by-product is reduced and the selectivity to acrylic acid that is mainly produced is enhanced, leading to sufficient restoration of the catalytic performance.

The invention claimed is:

1. A method comprising a contacting step of bringing a solid catalyst containing a component that forms a molten salt in the presence of steam into contact with oxygen and steam,
    wherein the steam in the contacting step has a partial pressure of 0.3 to 10 MPa.

2. The method according to claim 1,
    wherein the component that forms a molten salt contains a condensed phosphate.

3. The method according to claim 1,
    wherein the contacting step is performed at 200° C. to 700° C.

4. The method according to claim 2,
wherein the contacting step is performed at 200° C. to 700° C.

5. The method according to claim 2,
wherein the condensed phosphate is a mixture of an alkali metal salt and an alkaline-earth metal salt.

6. The method according to claim 2,
wherein the condensed phosphate is at least one compound selected from the group consisting of $Na_4P_2O_7$, $Na_2H_2P_2O_7$, $(NaPO_3)_n$, $K_4P_2O_7$, $K_2H_2P_2O_7$, $(KPO_3)_n$, $Ca_2P_2O_7$, $CaH_2P_2O_7$, $Ca(PO_3)_2$, $Ca_3(PO_4)_2$, $Ba_2P_2O_7$, $BaH_2P_2O_7$, $Ba(PO_3)_2$, $Ca_{2-x-s}K_{2x}H_{2s}P_2O_7$ and $Ba_{2-x-s}K_{2x}H_{2s}P_2O_7$,
wherein n is a positive integer, x and s are each 0 or more and less than 0.5.

7. The method according to claim 2,
wherein the condensed phosphate is at least one compound selected from the group consisting of $K_4P_2O_7$, $K_2H_2P_2O_7$, $(KPO_3)_n$, $Ba_2P_2O_7$, $BaH_2P_2O_7$, $Ba(PO_3)_2$ and $Ba_{2-x-s}K_{2x}H_{2s}P_2O_7$,
wherein n is a positive integer, x and s are each 0 or more and less than 0.5.

8. The method according to claim 2,
wherein the condensed phosphate is at least one compound selected from the group consisting of $Ba_2P_2O_7$, $(KPO_3)_n$ and $Ba_{2-x-s}K_{2x}H_{2s}P_2O_7$,
wherein n is a positive integer, x and s are each 0 or more and less than 0.5.

9. The method according to claim 2,
wherein the condensed phosphate is a mixture of $Ba_2P_2O_7$ and $(KPO_3)_n$.

10. The method according to claim 2,
wherein when a mixture of an alkali metal salt and an alkaline-earth metal salt is used as the condensed phosphate, the molar ratio of the alkali metal to the alkaline-earth metal (alkali metal/alkaline-earth metal) is 0.5 to 2.0.

11. The method according to claim 1,
wherein the solid catalyst is supported on a carrier, and
wherein the carrier is at least one selected from the group consisting of silica, diatomite, alumina, silica alumina, silica magnesia, zirconia, titania, magnesia, niobia, ceria, zeolite, silicon carbide and carbide.

12. The method according to claim 1,
wherein the steam in the contacting step has a partial pressure of 0.3 to 5.0 MPa.

13. The method according to claim 1,
wherein the steam in the contacting step has a partial pressure of 0.3 to 1.0 MPa.

14. The method according to claim 1,
wherein the oxygen partial pressure is more than 0 MPa and not more than 1.0 MPa.

15. The method according to claim 1,
wherein the oxygen concentration in the gas component other than steam in the contacting step is 50% by volume or less.

16. The method according to claim 1,
wherein the amount of the steam in the contacting step relative to 100% by volume of oxygen is 1% to 100000% by volume.

17. The method according to claim 1,
wherein the contacting step is performed at 250° C. to 650° C.

18. The method according to claim 1,
wherein the contacting step is performed at 300° C. to 600° C.

* * * * *